US009980651B2

(12) United States Patent
Pfeiffer et al.

(10) Patent No.: US 9,980,651 B2
(45) Date of Patent: May 29, 2018

(54) METHOD FOR THE OPTICAL THREE-DIMENSIONAL MEASUREMENT OF A DENTAL OBJECT

(75) Inventors: Joachim Pfeiffer, Bensheim (DE); Frank Thiel, Ober-Ramstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 542 days.

(21) Appl. No.: 14/124,597

(22) PCT Filed: Jun. 13, 2012

(86) PCT No.: PCT/EP2012/061154
§ 371 (c)(1),
(2), (4) Date: Dec. 6, 2013

(87) PCT Pub. No.: WO2012/171935
PCT Pub. Date: Dec. 20, 2012

(65) Prior Publication Data
US 2014/0104406 A1   Apr. 17, 2014

(30) Foreign Application Priority Data
Jun. 15, 2011   (DE) .................. 10 2011 077 564

(51) Int. Cl.
H04N 9/47        (2006.01)
H04N 7/18        (2006.01)
(Continued)

(52) U.S. Cl.
CPC .......... *A61B 5/0088* (2013.01); *A61B 5/1076* (2013.01); *A61B 5/1077* (2013.01);
(Continued)

(58) Field of Classification Search
CPC .................................................. A61C 9/006
(Continued)

(56) References Cited

U.S. PATENT DOCUMENTS 4,511,252 A    4/1985   Di Matteo et al. ........... 356/375
5,372,502 A *  12/1994  Massen .................. G01B 11/24
                                                    433/215
(Continued)

FOREIGN PATENT DOCUMENTS

CN    101862182 A    10/2010
DE    38 29 925 A1    3/1990
(Continued)

OTHER PUBLICATIONS

International Search Report from International Application No. PCT/EP2012/061154, dated Jan. 3, 2013.
(Continued)

*Primary Examiner* — Hung Dang
*Assistant Examiner* — Girumsew Wendmagegn
(74) *Attorney, Agent, or Firm* — Fitzpatrick, Cella, Harper & Scinto

(57) ABSTRACT

The invention relates to a method for the optical three-dimensional measurement of a dental object, wherein a first region of the dental object is measured using a first optical three-dimensional measurement method, wherein the first optical three-dimensional measurement method is based on a triangulation method and on a fringe projection method. According to the invention, a powdering occurs at least on the first region, wherein first image data are generated. Using a less precise, second optical three-dimensional measurement method, a second region of the dental object is subsequently measured without previous powdering, wherein second image data are generated. Afterwards, the first image data are combined with the second image data to form an overlapping three-dimensional exposure.

24 Claims, 3 Drawing Sheets

(51) Int. Cl.
*A61B 1/04* (2006.01)
*A61B 5/00* (2006.01)
*G01B 11/24* (2006.01)
*G01B 9/02* (2006.01)
*G01B 11/25* (2006.01)
*A61C 9/00* (2006.01)
*A61B 5/107* (2006.01)
*A61C 1/08* (2006.01)
*A61C 19/04* (2006.01)
*G06T 7/00* (2017.01)
*G06T 11/60* (2006.01)
*A61C 13/00* (2006.01)

(52) U.S. Cl.
CPC .......... *A61B 5/1079* (2013.01); *A61B 5/4547* (2013.01); *A61C 1/088* (2013.01); *A61C 9/006* (2013.01); *A61C 9/0073* (2013.01); *A61C 19/04* (2013.01); *G01B 9/0209* (2013.01); *G01B 11/2441* (2013.01); *G01B 11/2513* (2013.01); *G06T 7/0012* (2013.01); *G06T 11/60* (2013.01); *A61C 13/0004* (2013.01)

(58) Field of Classification Search
USPC .......................................................... 348/77
See application file for complete search history.

(56) References Cited

U.S. PATENT DOCUMENTS

| | | | | |
|---|---|---|---|---|
| 5,471,303 | A | 11/1995 | Ai et al. | 356/357 |
| 6,344,898 | B1 | 2/2002 | Gemma et al. | 356/513 |
| 6,813,035 | B2 | 11/2004 | Hoffmann | 356/603 |
| 7,006,126 | B2 | 2/2006 | Kerschnaumer et al. | 348/66 |
| 7,142,310 | B2 | 11/2006 | Straehle | 356/497 |
| 7,315,383 | B1 | 1/2008 | Abdollahi | 356/601 |
| 7,388,678 | B2 | 6/2008 | Forster et al. | 356/603 |
| 7,573,583 | B2 | 8/2009 | Quadling et al. | 356/602 |
| 7,986,415 | B2 | 7/2011 | Thiel et al. | 356/608 |
| 8,160,334 | B2 | 4/2012 | Thiel et al. | |
| 8,488,113 | B2 | 7/2013 | Thiel et al. | 356/73 |
| 2002/0080366 | A1 | 6/2002 | Nakayama | 356/512 |
| 2002/0196438 | A1 | 12/2002 | Kerschbaumer et al. | 356/327 |
| 2003/0002052 | A1 | 1/2003 | Hoffmann | 356/603 |
| 2004/0179203 | A1 | 9/2004 | Straehle | 356/497 |
| 2006/0098212 | A1 | 5/2006 | Forster et al. | 356/604 |
| 2007/0090308 | A1 | 4/2007 | Harding | 250/559.42 |
| 2007/0194214 | A1 | 8/2007 | Pfeiffer | 250/216 |
| 2009/0279103 | A1 | 11/2009 | Thiel et al. | 356/608 |
| 2010/0253773 | A1 | 10/2010 | Oota et al. | 348/77 |
| 2010/0268029 | A1 | 10/2010 | Phan et al. | |
| 2010/0268069 | A1 | 10/2010 | Liang | |
| 2010/0309301 | A1 | 12/2010 | Thiel et al. | 348/77 |
| 2010/0311005 | A1* | 12/2010 | Liang | A61B 1/00009 433/29 |
| 2011/0075159 | A1 | 3/2011 | Chang et al. | 356/625 |
| 2011/0080576 | A1 | 4/2011 | Thiel et al. | 356/73 |
| 2011/0287387 | A1 | 11/2011 | Chen et al. | |

FOREIGN PATENT DOCUMENTS

| | | |
|---|---|---|
| DE | 199 44 021 A1 | 5/2000 |
| DE | 199 63 333 A1 | 7/2001 |
| DE | 103 02 055 A1 | 8/2004 |
| DE | 10 2007 005 7 | 8/2008 |
| DE | 10 2009 021 136 A1 | 12/2010 |
| EP | 0 288 983 A2 | 11/1988 |
| EP | 1 229 350 A2 | 8/2002 |
| EP | 1 262 751 A2 | 12/2002 |
| EP | 2 175 232 A1 | 4/2010 |
| EP | 2 241 247 A1 | 10/2010 |
| EP | 2 258 254 A1 | 12/2010 |
| EP | 2 327 372 A1 | 6/2011 |
| FR | 2 635 965 A1 | 3/1990 |
| JP | 2010-246899 A | 11/2010 |
| JP | 2011-504230 A | 2/2011 |
| WO | WO 2004/010076 A1 | 1/2004 |
| WO | WO 2004/085956 A1 | 10/2004 |
| WO | WO 2009/071611 A2 | 6/2009 |
| WO | WO 2009/121922 A1 | 10/2009 |
| WO | WO 2013/008097 A1 | 1/2013 |

OTHER PUBLICATIONS

English language translation of International Search Report from International Application No. PCT/EP2012/061154, dated Jan. 3, 2013.

PresseBox, "JPK Instruments, die Pioniere des BioAFM, stellen die neue Generation des NanoWizard(R) Rasterkraftmikroskops (AFM) vor", Jun. 29, 2010, with machine translation.

German Patent Office, Office Action dated Sep. 12, 2011, issued in connection with German Appl'n No.10 2011 077 564.1, with machine translation.

Int'l Searching Authority, Int'l Search Report and Written Opinion dated Jan. 3, 2013, issued in connection with Int'l Appl'n No. PCT/EP2012/061154, with translation.

German Patent Office, Office Action dated Dec. 12, 2013, issued in connection with German Appl'n No. 10 2011 077 564.1, with machine translation.

Office Action issued in Japanese Patent Application No. 2014-515166, dated Mar. 15, 2016.

* cited by examiner

METHOD FOR THE OPTICAL THREE-DIMENSIONAL MEASUREMENT OF A DENTAL OBJECT

CROSS REFERENCE TO RELATED APPLICATION

The present application is a national-stage entry under 35 U.S.C. § 371 of International Application No. PCT/EP2012/061154 filed on Jun. 13, 2012, and claims the benefit of foreign priority under 35 U.S.C. § 119(a)-(d) of German Application No. 10 2011 077 564.1, filed on Jun. 15, 2011. Each of those applications is hereby incorporated by reference as if set forth fully herein.

TECHNICAL FIELD

The invention relates to a method for three-dimensional optical measurement of a dental object, wherein a first region of the dental object is measured using a first three-dimensional optical measurement method, wherein a powder is applied in at least the first region, and wherein first image data are generated.

PRIOR ART

Several methods for three-dimensional optical measurement of a dental object are known from the prior art. Three-dimensional optical methods in particular, such as the triangulation method, the confocal microscopy method or the white light interferometry method are already known.

DE 199 63 333 A1 discloses another three-dimensional optical method in which a color pattern of a known structure consisting of multiple pattern elements is projected onto the project. This projected color pattern is photographed, wherein a projection angle is assigned to each of the pattern elements in an additional process step; at this projection angle, the three-dimensional coordinates of observed object points can be ascertained when the relative position between the camera and projector is known.

WO 2004/010076 A1 discloses a refinement of this method, in which the projection data of the color pattern are coded using a redundant code.

With the known fringe projection method, the object for measurement is illuminated from parallel light and dark fringe of different widths. In another step, the projected fringe pattern is photographed by means of a camera at a known angle of view with respect to the projection. Using a so-called phase shift method, a projection coordinate that reflects the number of the fringe is determined. The number of the fringe in the projector corresponds to an image coordinate in the camera. With a known camera position and a known projector position relative to the object, the point of intersection specified by the respective fringe and the straight line specified by the coordinate in the camera can be calculated. The three-dimensional coordinates of the surface are determined for each of the measurement points in this way.

Light of a low coherence length is used in white light interferometry, resulting in color indifferences when the path lengths in the reference beam and the object beam are almost the same. The interference pattern changes with a change in path length, which means that the distance to the surface of the object for measurement can be determined on the basis of the interference pattern.

In the three-dimensional confocal microscopy method, the surface of the dental object is scanned incrementally, while a focal plane is shifted incrementally. Light outside of the focal plane is masked out as much as possible by means of an aperture. Then a three-dimensional model of the measured object can be calculated from the measured image data of the individual steps.

One disadvantage of the fringe projection method is that a non-reflective surface of the measured object is required for an accurate photograph. The dental object is therefore usually coated with a special powder before the photograph is taken. The applied powder layer is removed after the photograph has been taken.

Merely low precision is achieved without the application of powder, because photographic errors are created due to uneven reflections.

The other three-dimensional optical methods mentioned above without the prior application of powder offer only inadequate precision for certain applications such as measuring a preparation area for planning a dental restoration.

However, there are measurement tasks for which the highest possible measurement precision is not necessary. Such measurement tasks include, for example, measurement of the entire jaw, measurement of the opposing teeth in a preparation region and overview photographs.

The object of the present invention is therefore to provide a method for three-dimensional optical measurement of a dental object, wherein a rapid and simple measurement is made possible with adequate accuracy of the respective measurement task.

DESCRIPTION OF THE INVENTION

The invention relates to a method for three-dimensional optical measurement of a dental object, wherein a first region of the dental object is measured using a first three-dimensional optical measurement method. The first three-dimensional optical measurement method is based on a triangulation method and on a fringe projection method. Before the measurement is performed, powder is applied at least to the first region, wherein first image data are generated. Then using a second three-dimensional optical measurement method that is less precise, a second region of the dental object is measured without powder first being applied, thereby generating second image data. The first image data are then combined with the second image data to form a superimposed three-dimensional photograph.

The first three-dimensional optical measurement method permits a precise measurement of the dental object with the smallest possible deviations from the actual dimensions of the object and may be, for example, the trigonometric fringe projection method with the prior application of powder to the object. The first region requires a precise measurement and may include, for example, a preparation and neighboring teeth near this preparation for insertion of a planned restoration. The first image data comprise a three-dimensional structure of the first region of the dental object and may be stored in a memory. The second three-dimensional optical measurement method has less precision but can be performed more easily and more rapidly than the first measurement method. The advantages of the second measurement method in comparison with the first measurement method may include the fact that the second measurement method is less sensitive to shaking of the handpiece when the measurement is performed; application of powder to the object to prevent interfering reflections is not necessary; the fact that color information may be obtained from the object during the measurement; and the fact that the measurement is performed continuously during a fly-over movement (on-the-fly capacity) over the measured object and not incrementally through multiple individual photographs from different angles of space. The second image data generated may also be saved in a memory. Then the first image data are combined with the second image data by means of a computer to form a superimposed three-dimensional photograph having the required precision in the first region and in the second region of the dental object photographed.

One advantage of this method is that it provides a simple, rapid and optimized three-dimensional method that meets the accuracy requirements of this measurement task and is optimized for the specific measurement task.

Another advantage of this method is that deviations between the first image data and the second image data and therefore optical errors are detected when the two sets of image data are combined so that these errors can then be corrected.

Through the application of powder in the first measurement method, the first region, which may be a preparation site, is coated with powder to prevent reflection in a first step, and in a second step, it is measured by means of a dental handpiece by means of the fringe projection method. To improve the precision, shortwave blue light may be used in the first, precise measurement method to improve the precision of the photograph. Blue light with a wavelength of 400 nm to 500 nm may preferably be used.

The second region is measured by means of the second measurement method, which is less sensitive with respect to reflection, which means that the second region does not require a prior application of powder.

The second three-dimensional optical measurement method may advantageously correspond to the first three-dimensional optical measurement method, with the difference being that a grid period of a projection grid is larger and no powder is applied to the second region.

The second measurement method, like the first measurement method, is thus based on the fringe projection method, but the second grid period of the projection grid is larger in the second method than the first grid period of the projection grid in the first method, and it is not necessary to apply powder to the second region. The second measurement method is therefore less precise but may be simpler to perform. The first grid period of the projection grid may be between 300 µm and 400 µm, preferably 350 µm, and the second grid period of the projection grid may be between 600 µm and 800 µm, preferably 700 µm.

The second three-dimensional optical measurement method may advantageously be based on a confocal microscopy method.

The confocal microscopy method for three-dimensional measurement is less sensitive with respect to reflection at the surface of the object than the fringe projection method and thus permits a three-dimensional determination of shape without powder being applied to the object. The second region may therefore be measured by using the confocal microscopy method without powder being applied to it. The color of the object can also be detected with this method. The disadvantage of this method is that resolution, which depends on the dimensions of the confocal plane, is lower than with the fringe projection method and that the duration of the measurement is much longer than that in the fringe projection method.

The second three-dimensional optical measurement method may advantageously be based on a white light interferometry method.

The second region may therefore be measured by means of a dental handpiece, which is based on the white light interferometry method. The white light interferometry method is less sensitive with regard to reflection at the surface of the object, and therefore it permits a three-dimensional determination of the shape of the second region without the application of any powder. In addition to the three-dimensional measurement, color information about the surface of the object can also be obtained.

The second three-dimensional optical measurement method may advantageously be based on a triangulation method using color patterns.

The known triangulation method using color patterns has the advantage that the measurement does not require the prior application of powder to the second region, and additional color information about the dental object can be obtained.

In performing the second three-dimensional optical measurement method, color information about the dental object may advantageously be generated.

Therefore, in addition to the three-dimensional dimensions of the measured object, color information about the object can also be obtained. This color information about the second region, for example, the neighboring teeth, may be used for planning the restoration in order to match the shade of the planned restoration to that of the neighboring teeth.

The first region of the dental object may advantageously be a preparation site in a patient's oral cavity.

Therefore, using the first region photographed with the first, more precise measurement method includes the preparation site for inserting a restoration. The neighboring teeth, the opposing teeth, the remaining area of the jaw and/or the gingiva surrounding the preparation site may then be measured by means of the second, less precise measurement method.

The second region of the dental object may advantageously be an opposing tooth comprising a neighboring tooth adjacent to the first region or the entire jaw.

The aforementioned structures are therefore detected with less precision and serve only for orientation and planning of the restoration to be inserted, which is adapted in shape and/or in coloration to the neighboring teeth and the opposing teeth.

The second region may advantageously comprise the first region of the dental object.

The first region is therefore detected by means of the first measurement method as well as by means of the second measurement method, which is less precise.

The first image data may advantageously be compared with the second image data, and therefore faulty locations in the first image data are detectable.

Therefore, optical errors caused by the faulty application of powder to the first region, for example, can be detected. Shaking of the handpiece used during the measurement of the first region by means of the first measurement method may also result in errors in the photograph, which can be detected by comparison with the second image data.

The faulty locations in the first image data may advantageously be corrected.

The faulty locations can be corrected automatically using known pattern recognition algorithms or manually by the user. The result of the correction is an error-free photograph including both the first region and the second region.

The second region and the first region may advantageously not overlap.

The first region of the object is therefore measured using only the first measurement method.

Another subject matter of the invention is a measuring device for three-dimensional optical measurement of a dental object, comprising first means for use of a first, precise three-dimensional optical measurement method based on a triangulation method and based on a fringe projection method. The first means comprise a first projection grid with a first grid constant. The measuring device additionally comprises second means for use of a second, less precise three-dimensional optical measurement method. The measuring device also comprises a switch and adjustment means for switching the measuring device between a first mode for operation according to the first method and a second mode for operation according to the second method. During the switch from the first mode to the second mode by means of the adjustment means, the second means are arranged in the path of the beam of the measuring device instead of the first means.

The measuring device makes it possible to perform the above-mentioned inventive method. In the first mode, the dental object can be measured using the first, precise optical measurement method, and in the second mode, the dental object can be measured using the second, less precise optical measurement method. Depending on the mode set, the first means or the second means are introduced into the path of the beam of the measuring device. The first projection grid may have different projection patterns, such as parallel fringe. The switch is manually operable by a user.

One advantage of the measuring device is that the dental object can optionally be detected with the same measuring device by using the first measurement method or the second measurement method. Therefore, it is not necessary to change the measuring device, and so the duration of the entire measurement is shortened.

The second measurement method may advantageously correspond to the first measurement method except for the difference that the second means comprise a second projection grid with a second grid constant, which can be introduced into the path of the beam of the measuring device. The second grid constant of the second projection grid is larger than the first grid constant of the first projection grid.

The second measurement method with the larger grid constant leads to a lower resolution of the image data thereby generated than is the case with the first measurement method, but it has the advantage that it is not necessary to apply powder to the dental object to prevent reflection. The values of the grid constants relate to the distances between the parallel lines of the projection pattern in the plane of the object.

The first grid constant of the first projection grid in an object plane may advantageously be between 300 μm and 400 μm, preferably 350 μm. The second grid constant of the second projection grid in the plane of the object may be between 600 μm and 800 μm, preferably 750 μm.

During the switch from the first mode to the second mode, the second projection grid may advantageously be pivoted into the path of the beam at the location of the first projection grid by means of a mechanical pivoting device.

The mechanical pivoting device thus makes it possible to arrange the second means in the location of the first means in the path of the beam of the measuring device by switching in a simple operation. The mechanical pivoting device may have a pivot axle, for example, which is aligned parallel to the path of the beam of the measuring device, wherein the first means and the second means are pivotably connected to the pivot axle. The first and second means are rotated about a certain angle of rotation by the rotation of the pivot axle, such that they are optionally introduced into the path of the beam of the measuring device. The pivot axle may be driven by means of an electric motor such as a stepping motor, which is controlled by means of a control device accordingly.

The first and second projection grids may advantageously be generated by means of a digital light projector (abbreviated DLP). During the switch from the first mode to the second mode, the digital light projector is controlled by means of a control device, which means that the second projection grid is generated instead of the first projection grid, and a line pattern having the desired grid constant in the plane of the object is projected onto the object.

Rapid switching between the first and second modes is made possible by using the digital light projector. The digital light projector may have, for example, liquid crystal elements. One advantage is that no mechanical adjustment means are necessary for performing the switching, and therefore the lifetime and operational reliability of the measuring device are improved.

The second means may advantageously be suitable for use of a confocal microscopy method and may comprise a light source, a first aperture, a second aperture, a beam splitter and/or a detector. The second means are arranged in the second mode such that an illuminating beam emitted by the light source passes through the first aperture and is focused by means of the focusing device on a focal plane to be measured. The second aperture is arranged such that an observation beam reflected back by the object in the focal plane passes through the second aperture and reaches the detector, and the observation beams outside of the focal plane are masked out.

In the second mode, a measurement is therefore performed by means of the confocal microscopy method, permitting detection of the color of the dental object in addition to detection of the three-dimensional structure.

The second means may advantageously be suitable for use of a white light interferometry method and may comprise a broadband white light source as well as an interferometer.

The interferometer may have any desired design. The white light source has a broad spectrum, preferably continuous.

The second means for use of a triangulation method with color patterns may advantageously have multiple light sources of different colors or one light source with multiple filters of different colors and a projection grid for generating the projected color patterns.

Color patterns such as parallel lines of different colors, which are clearly differentiated from one another, may therefore be generated and projected onto the dental object. The same light source and the same projection grid may be used for the first mode and for the second mode, which means that color filters are pivoted into the path of the beam during the switch to the second mode. In such an advantageous embodiment, the light source has a broad spectrum with wavelengths of the colors used for the color pattern.

BRIEF DESCRIPTION OF THE DRAWINGS

The present invention is explained with reference to the drawings, in which.

EXEMPLARY EMBODIMENT

Figure 1:
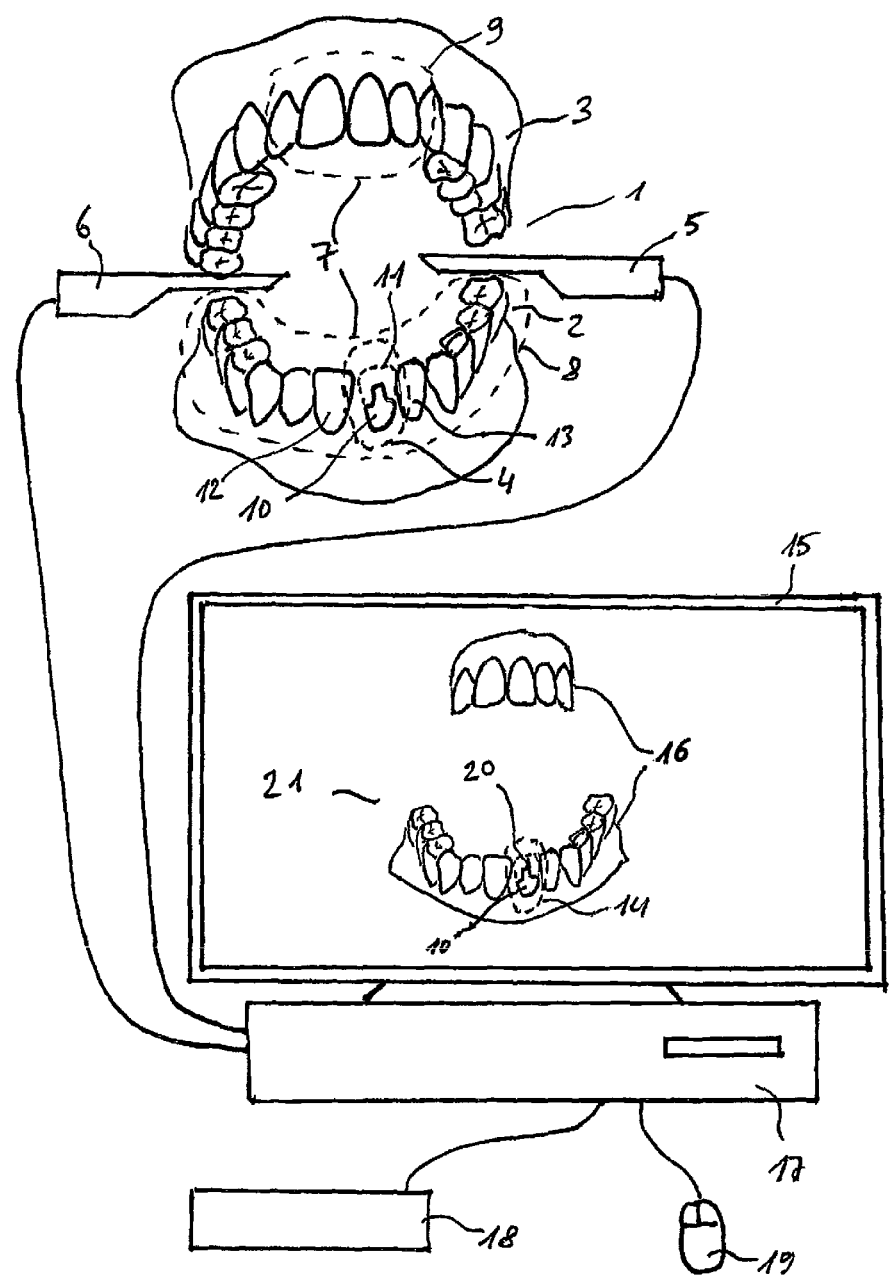
FIG. 1 shows a diagram of a device for performing the present with two handpieces.

FIG. 1 shows a diagram to illustrate the present method of three-dimensional optical measurement of a dental object 1, comprising a mandible 2 and a maxilla 3. The dental object 1 may also comprise only parts of the mandible 2 or of the maxilla 3. A first region 4 surrounded by a dotted line is measured using a first, precise measuring device 5, which is suitable for performing a first, precise three-dimensional optical measurement method. The first measuring device 5 may be a dental handpiece, wherein the first measurement method is based on a triangulation method and on a fringe projection method. Before the measurement by means of the first measuring device 5, the first region 4 is coated with a powder, which prevents light reflection, to improve the measurement accuracy. Then, by means of a second, less precise measuring device 6, a second region 7 of the dental object 1 is measured, comprising the entire lower row of teeth 8 and opposing teeth 9. The first region 4 may comprise, for example, a preparation 10 for a restoration 11 to be created. The first region 4 must be measured accurately to ensure an accurate fit of the restoration 11 on the preparation 10. The second measuring device 6 is suitable for use of a second, less precise, three-dimensional optical measurement method. Like the first measurement method, the second measurement method may be a fringe projection method, for example, except that it uses a projection grid with a larger grid period and without a prior application of powder. Other measurement methods, such as the confocal microscopy method or the white light interferometry method, may also be used as the second measurement method. The lower row of teeth 8 also includes neighboring teeth 12, 13. In planning the restoration 11, the shape and orientation of the preparation 10 photographed by means of the first measurement method and those of the neighboring teeth 12, 13 and of the opposing teeth 9 photographed by means of the second measurement method are used. During the measurement of the first region 4 by means of the first measuring device 5, first image data 14 of the first region are generated, as displayed by means of the display device 15. In the measurement of the second region 7 by means of the second measuring device 6, second image data 16 are generated and displayed in superpositioning with the first image data by means of the display device 15. The first image data 14 and the second image data 16 are transmitted to the computer 17 and compiled to yield a three-dimensional model, which can be observed from different angles of viewing by means of the display device 15. The first region 4 is covered by the second region 8 of the dental object 1, which means that the preparation cords are measured by means of the first measuring device 5 and also by means of the second measuring device 6. By comparison of the first image data 14 with the second image data 16, errors in the photograph in the region of the preparation can be detected and corrected. The correction may be corrected automatically using known pattern recognition methods or manually by the user by means of the input means, 18 and 19. The photographic error 20 may be, for example, an elevation created due to the inadequate application of powder and thus due to excessive reflection. This photographic error 20 can be detected by means of pattern recognition methods, or it can be marked manually by using the input means 18, 19. The first image data 14 of the first region and the second image data 16 of the second region 7 are combined to form a superimposed three-dimensional photograph 21, which is displayed by means of the display device 15.

Figure 2:
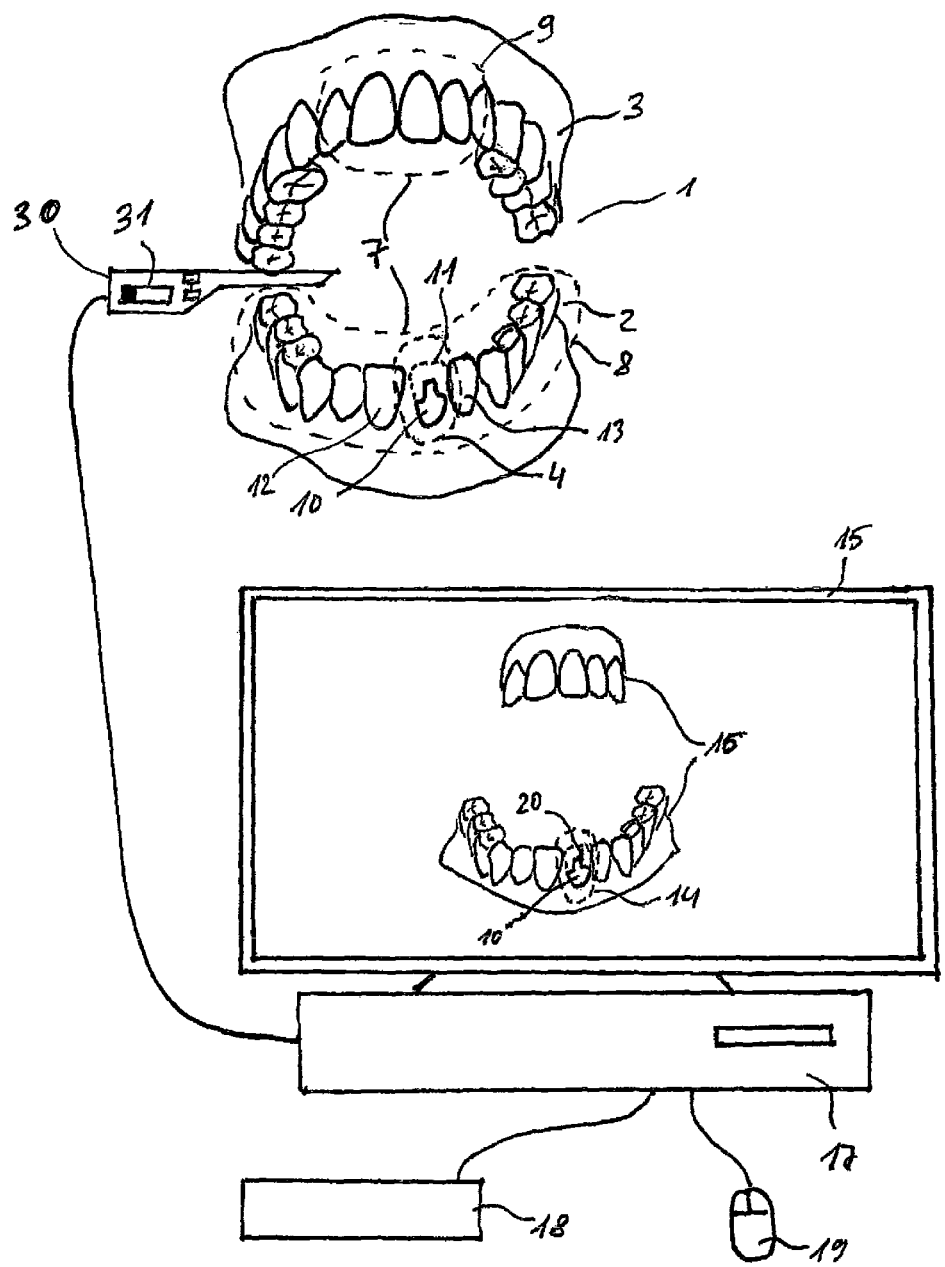
FIG. 2 shows a diagram of a device for performing the present with one handpiece.

FIG. 2 shows a device having a switch 31 for performing an alternative method, wherein a single measuring device 30 is used in comparison with the device from FIG. 1. The first, precise measurement method is used in the first mode of the measuring device 30, and the second, less precise measurement method is used in a second mode. In the first mode, the projection grid having a smaller grid period may be introduced into the path of the beam of the measuring device 30, but this requires the prior application of powder to the first region 4. In the second mode, a projection grid having a larger grid period is placed in the path of the beam of the measuring device 30, which means that the measurement can be performed in the second mode even without a prior application of powder. In the first step, the measuring device is used in the first mode for measuring the first region 4. In the second step, the measuring device is switched to the second mode and used to measure the second region 7 of the dental object 1.

Figure 3:
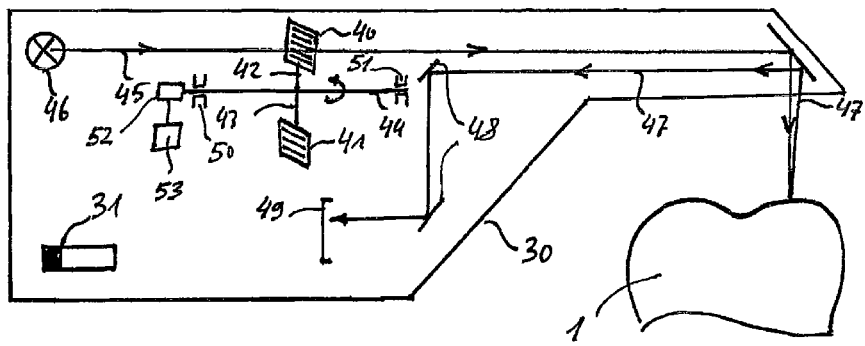
FIG. 3 shows a diagram of a first embodiment of the measuring device from FIG. 2.

FIG. 3 shows an embodiment of the measuring device 30 from FIG. 2, which has a first projection grid 40 with a first grid constant of 350 μm and a second projection grid 41 with a larger grid constant of 700 μm. The first projection grid 40 and the second projection grid 41 are pivotably connected to a pivot axle 44 by the webs, 42 and 43. The pivot axle 44 is arranged in parallel with a beam path 45 of an illumination beam emitted by a first light source 46. When the switch 31 is operated, the measuring device 30 is switched to the first mode into the second mode. The pivot axle 44 is then rotated by 180°, which means that the second grid 41 is positioned in the beam path 45 of the illuminating beam. Therefore, the dental object 1, such as a single tooth or a group of teeth, can be measured in the second mode using the second method with the larger grid constant. During the switch from the second mode to the first mode, the pivot axle 44 is rotated by 180° again, which means that the first projection grid 40 is again positioned in the beam path 45. The observation beam 47 reflected by the dental object 1 is deflected to a detector 49 by means of two beam deflectors 48. Then a three-dimensional photograph of the dental object 1 is created from the image data thereby generated. The pivot axle 44 is rotatably mounted in a first bearing 50 and a second bearing 51, wherein the bearings, 50 and 51, may be ball bearings. The pivot axle 44 is driven by means of an electric motor 52 such as a stepping motor, which is controlled by means of a motor control 53 accordingly when the switch 31 is operated.

Figure 4:
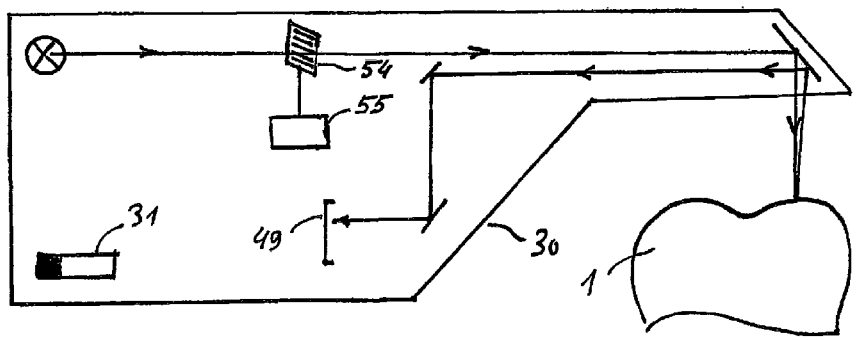
FIG. 4 shows a diagram of a second embodiment of the measuring device from FIG. 2.

FIG. 4 shows another embodiment of the measuring device 30 from FIG. 2, wherein this embodiment differs from the embodiment illustrated in FIG. 3 in that the first and second projection grids are generated by a digital light projector 54, which is controlled by a control device 55 accordingly when the switch 31 is switched to the first mode or to the second mode. The digital light projector 54 may comprise liquid crystal elements (LCD).

Figure 5:
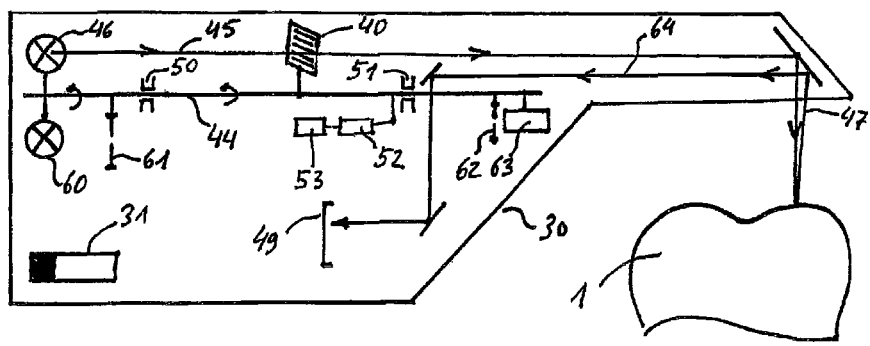
FIG. 5 shows a diagram of a third embodiment of the measuring device from FIG. 2.

FIG. 5 shows another embodiment of the measuring device 30 from FIG. 2, wherein the second method is a confocal microscopy method. The first means for the first mode are arranged on the first top side of the pivot axle 44, and the second means for the second mode are arranged on the second bottom side of the pivot axle 44. In switching the measuring device 30 from the first mode to the second mode, the pivot axle 44 is rotated by 180°, which means that the second means enter the beam path 45 of the measuring device 30. The first means for the first mode comprise a first light source 46 and the first projection grid 40. The second means comprise a second light source 60 and a first aperture 61, a second aperture 62 and a focusing device 63. The second light source 60 may be a monochromatic light source, such as a laser. In switching to the second mode by rotating the pivot axle 44 by 180°, the second light source 60 reaches the position of the first light source 46, the first aperture 61 enters the beam path 41, [and] the second aperture and the focusing device 63 enter a beam path 64 of the observation beam 47. Therefore, measurement of the dental object 1 using the confocal microscopy method is made possible in the second mode. The pivot axle 44 is rotatably mounted in a first bearing 50 and a second bearing 51, as in the first embodiment in FIG. 3, wherein the bearings, 50 and 51, may be ball bearings. The pivot axle 44 is driven by means of an electric motor 52, such as a stepping motor, which is controlled by means of a motor control 53 accordingly.

The invention claimed is:

1. A method of measuring a dental object, comprising:
   measuring a first region of a dental object using a first three-dimensional optical measurement method to generate first image data of the first region of the dental object, wherein the first three-dimensional optical measurement method is based on a triangulation method and on a fringe projection method, and wherein the first region of the dental object is coated with a powder that minimizes light reflection;
   measuring a second region of the dental object using a second three-dimensional optical measurement method to generate second image data of the second region of the dental object, wherein a portion of the second region of the dental object is not coated with the powder that minimizes light reflection; and
   combining the first image data and the second image data to form a superimposed three-dimensional image.

2. The method according to claim 1, wherein the second three-dimensional optical measurement method uses a projection grid with a larger grid period than a projection grid used in the first three-dimensional optical measurement method.

3. The method according to claim 1, wherein the second three-dimensional optical measurement method is a confocal microscopy method.

4. The method according to claim 1, wherein the second three-dimensional optical measurement method is a white light interferometry method.

5. The method according to claim 1, wherein the second three-dimensional optical measurement method is a triangulation method using color patterns.

6. The method according to claim 1, wherein color information about the dental object is generated in the measuring of the second region of the dental object.

7. The method according to claim 1, wherein the first region of the dental object is a preparation site in a patient's oral cavity.

8. The method according to claim 1, wherein the second region of the dental object comprises: an opposing tooth, a neighboring tooth in proximity to the first region of the dental object, or an entire jaw.

9. The method according to claim 1, wherein the second region of the dental object comprises the first region of the dental object.

10. The method according to claim 1, further comprising: comparing the first image data with the second image data to detect faulty locations in the first image data.

11. The method according to claim 10, further comprising: correcting the faulty locations in the first image data.

12. The method according to claim 1, wherein the second region of the dental object and the first region of the dental object do not overlap with one another.

13. A system for measuring a dental object, comprising:
   a first measuring device configured to measure a first region of a dental object using a first three-dimensional optical measurement method to generate first image data, wherein the first three-dimensional optical measurement method is based on a triangulation method and on a fringe projection method, and wherein the first region of the dental object is coated with a powder that minimizes light reflection;
   a second measuring device configured to measure a second region of the dental object using a second three-dimensional optical measurement method to generate second image data of the second region of the dental object, wherein a portion of the second region of the dental object is not coated with the powder that minimizes light reflection; and
   a computer configured to:
      combine (i) the first image data generated by the first measuring device, and (ii) the second image data generated by the second measuring device to form a superimposed three-dimensional image.

14. The system according to claim 13, wherein the second three-dimensional optical measurement method uses a projection grid with a larger grid period than a projection grid used in the first three-dimensional optical measurement method.

15. The system according to claim 13, wherein the second three-dimensional optical measurement method is a confocal microscopy method.

16. The system according to claim 13, wherein the second three-dimensional optical measurement method is a white light interferometry method.

17. The system according to claim 13, wherein the second three-dimensional optical measurement method is based on a triangulation method using color patterns.

18. The system according to claim 13, wherein the second image data comprises color information about the dental object.

19. The system according to claim 13, wherein the first region is a preparation site in a patient's oral cavity.

20. The system according to claim 13, wherein the second region comprises: an opposing tooth, a neighboring tooth in proximity to the first region of the dental object, or an entire jaw.

21. The system according to claim 13, wherein the second region of the dental object comprises the first region.

22. The system according to claim 13, wherein the computer is further configured to compare the first image data with the second image data to detect faulty locations in the first image data.

23. The system according to claim 22, wherein the computer is further configured to correct the faulty locations in the first image data.

24. The system according to claim 13, wherein the second region of the dental object and the first region of the dental object do not overlap with one another.

* * * * *